United States Patent [19]

Moo-Young et al.

[11] Patent Number: 5,651,973
[45] Date of Patent: Jul. 29, 1997

[54] THERAPEUTICALLY EFFECTIVE TOPICAL APPLICATION OF ST1435

[75] Inventors: Alfred Moo-Young, Hastings-on-Hudson, N.Y.; Ana Zepeda-Ortega; Horacio Bruno Croxatto, both of Santiago, Chile

[73] Assignee: The Population Council, New York, N.Y.

[21] Appl. No.: 952,867

[22] PCT Filed: May 24, 1991

[86] PCT No.: PCT/US91/03697

§ 371 Date: Nov. 30, 1992

§ 102(e) Date: Nov. 30, 1992

Related U.S. Application Data

[63] Continuation-in-part of Ser. No. 532,215, Jun. 1, 1990, abandoned.

[51] Int. Cl.$^6$ .................................................. A61K 9/06
[52] U.S. Cl. ........................ 424/401; 424/443; 424/448; 424/449; 514/841; 514/843; 514/944; 514/946; 514/947; 514/953
[58] Field of Search .............................. 424/443, 448, 424/449, 401; 514/841, 843, 944, 946, 947, 953; 604/304, 307; 128/830, 839, 840

[56] References Cited

U.S. PATENT DOCUMENTS

| | | | |
|---|---|---|---|
| 3,510,556 | 5/1970 | Erb et al. | 424/240 |
| 3,854,480 | 12/1974 | Zaffaroni | 128/260 |
| 3,948,262 | 4/1976 | Zaffaroni | 128/260 |
| 4,144,317 | 3/1979 | Higuchi et al. | 424/21 |
| 4,292,965 | 10/1981 | Nash et al. | 128/260 |
| 4,379,454 | 4/1983 | Campbell et al. | 604/897 |
| 4,818,540 | 4/1989 | Chien et al. | 424/448 |
| 4,834,978 | 5/1989 | Nuwayser | 424/448 |
| 4,911,916 | 3/1990 | Cleary | 424/449 |
| 4,913,905 | 4/1990 | Fankhauser et al. | 424/449 |
| 5,122,382 | 6/1992 | Gale et al. | 424/449 |

FOREIGN PATENT DOCUMENTS

| | | |
|---|---|---|
| 1532388 | 10/1988 | Australia. |
| 0370220 | 5/1990 | European Pat. Off.. |
| 1091660 | 11/1967 | United Kingdom. |
| 1292545 | 10/1972 | United Kingdom. |
| 9118572 | 12/1991 | WIPO. |

OTHER PUBLICATIONS

Pertti Lähteenmäki, "Contraceptive Action of A Synthetic Progestin," ST-1435, Steroid Research Laboratory, Department of Medical Chemistry, Univ. of Helsinki, pp. 12-44, (1986).

Pertti Lähteenmäki, "Pituitary and Ovarian Function During Contraception With One Subcutaneous Implant Releasing a Progestin, ST-1435", Contraception, vol. 25. No. 3, pp. 299-306, Mar. (1982).

Whitehead et al., "Endometrial Responses to Transdermal Estradiol in Postmenopausal Women", Am. J. Obstet. Gynecol, 152, 8:1079-1084 (1985).

Ahmed et al., "Transdermal Testosterone Therapy in the Treatment of Male Hypogonadism", J. Clin. Endocrinol. and Metab., 66, 3:546-551 (1988).

Sitruk-Ware, "Innovative Technology for Hormonal Replacement Therapy", Maturitas, 10:79-81 (1988).

(List continued on next page.)

*Primary Examiner*—Jyothsna Venkat
*Attorney, Agent, or Firm*—Brumbaugh, Graves, Donohue & Raymond

[57] ABSTRACT

The progesterone analog ST1435 has now been found to attain therapeutically effective levels upon topical application to the skin. ST1435 can be administered topically either in liquid or semisolid base such as a cream or gel or in a solid base such as a transdermal device such as a disk, band patch or bracelet. The invention further provides topical applications suitable for transdermal delivery of therapeutically effective amounts of ST1435.

11 Claims, 12 Drawing Sheets

OTHER PUBLICATIONS

Sitruk–Ware et al., "Treatment of Benign Breast Diseases by Progesterone Applied Topically", In: Percutaneous Absorption of Steroids, Mauvais–Jarvis et al., eds. London, England: Academic Press, pp. 219–229 (1980).

Mauvais–Jarvis et al., "In vivo Studies on Progesterone Metabolism by Human Skin", J. Clin. Endocrinol. Metab., 29:1580–1585 (1969).

Lähteenmäki et al., "Pituitary and Ovarian Function During Contraception With One Subcutaneous Implant Releasing a Progestin, ST–1435", Contraception, 25,3:299–306 (1982).

Coutinho et al., "Fertility Control With Sub–Dermal Silastic Capsules Containing a New Progestin (ST–1435)", Int. J. Fertil., 21:103–108 (1976).

Lähteenmäki et al., "Contraception With Subcutaneous Capsules Containing ST–1435. Pituitary and Ovarian Function and Plasma Levels of ST–1435", Contraception, 23,1:63–75 (1981).

Lähteenmäki et al., "Contraceptive Action of a Synthetic Progestin, ST–1435", Thesis, University of Helsinki, Helsinki, Finland, pp. 35–36 (1986).

Lähteenmäki, "Intestinal Absorption of ST–1435 in Rats", Contraception, 30,2:143–151 (1984).

World Health Organization (WHO), "The WHO Programme for the Standardization and Quality Control of Radioimmunoassay of Hormones in Reproductive Physiology", Horm. Res. 9:440–449 (1978).

Laurikka–Routti et al., "Suppression of Ovarian Function with the Transdermally Given Synthetic Progestin ST 1435", Fertility and Sterility, 58,4:680–684 (1992).

Haukkama et al., "Transdermal Absorption of the Progestin ST–1435: Therapeutic Serum Steroid Concentrations and High Excretion of the Steroid in Saliva", Contraception, 44,3:269–276 (1991).

Suhonen et al, "Endometrial Effect of Transdermal Estradiol and Progestin ST–1435 in Postmenopausal Women", Fertility and Sterility, 57,6:1211–1215 (1992).

THERAPEUTICALLY EFFECTIVE TOPICAL APPLICATION OF ST1435

This application is a national phase application of PCT Application No. PCT/US91/0367, filed May 24, 1991, which in turn claims priority from corresponding U.S. application Ser. No. 07/532,215, filed Jun. 1, 1990, now abandoned. The research disclosed in this application was conducted pursuant to an agreement with the U.S. Agency for International Development and, therefore, the U.S. Government has certain rights in the invention.

BACKGROUND OF THE INVENTION

This invention relates to a method of contraception. It has now been found that the transdermal application of the progestin analog ST1435 to the skin (hereinafter "topical application") is effective in attaining therapeutically effective serum levels of ST1435.

The most common form of hormonal contraception is oral contraceptives, which are widely popular as one of the most effective means of contraception available. Oral contraceptives usually contain a combination of the hormones estrogen and progestin. Unfortunately, natural hormones and many synthetic hormones are unsuited to oral administration. Most hormones suffer some degradation in the digestive tract and many are rapidly degraded by the liver in the so-called hepatic first-pass metabolism. Since even synthetic hormones may be metabolized to some extent during absorption, a large excess of hormone is frequently administered. Decreasing the dosage of hormones would have the effect of decreasing the risk of side effects but would decrease the efficacy of the hormones. A synthetic estrogen such as ethinylestradiol is ordinarily used as the estrogen component in oral contraceptives since less than ten percent of the natural estrogen, 17-β-estradiol, survives hepatic first-pass metabolism. In contrast, approximately 40% of ethinylestradiol survives hepatic first pass metabolism. Likewise, natural progesterone is ineffective when given orally except in micronized form and in large doses. Additionally, many synthetic hormones are unsuited to oral administration; for instance, the synthetic progestin ST1435 (16-methylene-17-α-acetoxy-19-nor-4-pregnene-3,20-dione) is ineffective when given orally due to rapid first-pass metabolism.

In order to circumvent hepatic metabolism, methods of hormone administration involving implants and topical applications have been developed. A typical implantable device is described in U.S. Pat. No. 3,854,480 issued Dec. 17, 1974 to Zaffaroni. Such a device consists of an inner core within which solid particles of drug are dispersed and an outer membrane that surrounds the inner core. The inner core is relatively permeable to the hormone and the outer membrane is relatively impermeable. The outer membrane thus regulates the rate of hormone delivery from the implant. Such implants are normally placed under the skin and have the advantage of prolonged drug release at a controlled rate.

The feasibility of a topical delivery system for contraception was realized when it was shown that testosterone, testosterone conjugates and estradiol could be absorbed through the skin. Topical delivery of contraceptive steroids has potential advantages over some of the present contraceptive dosage forms that are available to the public. Such advantages include: convenience of application and removal by the user; avoidance of hepatic first-pass metabolism and gastrointestinal incompatibility; controlled sustained release of the contraceptive drugs; maintenance of a steady-state plasma level of the drug(s), resulting in enhanced efficacy; and reduced frequency of dosing, as compared to daily oral contraception.

The advantages of topical administration of steroids have been widely acknowledged in recent years. Estradiol is used routinely in commercial preparations for the relief of post-menopausal symptoms. Whitehead et al., "Endometrial Responses to Transdermal Estradiol in Postmenopausal Women", Am. J. Obstet. Gynecol., 152:1079–1084 (1985). It has also been shown that transdermally administered testosterone is effective in long-term treatment of male hypogonadism. Ahmed et al., "Transdermal Testosterone Therapy in the Treatment of Male Hypogonadism", J. Clin. Endocrinol. Metab., 66:546–551 (1988).

Known topical applications for hormones are comprised of hormone dissolved or suspended in any of several liquid, semisolid, or solid vehicles. Liquid and semisolid vehicles have heretofore been used for therapeutic but not contraceptive administration of hormones. Such vehicles include but are not limited to gels, creams, ointments and rinses in which the hormone is at least somewhat soluble. A hormone should be at least partially soluble in the vehicle to facilitate delivery. Solid vehicles containing hormones are available, such as the "patch" described in U.S. Pat. No. 4,818,540, issued Apr. 4, 1989 to Chien et al. Such a transdermal device consists of the following elements: a backing layer relatively impervious to the hormone; a polymer matrix disk layer in which the hormone is dispersed; and an adhesive layer that adheres the device to the skin and allows the hormone to be absorbed transdermally.

Topical applications generally require administration of a lower concentration of the hormone than do oral dosages and are relatively easy to apply. Transdermal devices are useful for several days before the device must be changed. However, use of such devices for more than a few days in one location results in irritation and may cause dermatitis due to occlusion of the skin. The efficacy of transdermal applications is also determined in part by the thickness of the stratum corneum and hydration of the skin which affect diffusion of steroids through the skin. Sitruk-Ware, "Innovative Technology for Hormonal Replacement Therapy", Maturitas, 10:79–81 (1988).

Skin occlusion is a serious drawback to the use of transdermal patches. Occlusion occurs when the skin is blocked so that the passage of any gases or moisture through the skin is prevented.

Occlusion of the skin for the short term (a few days) is not harmful and may be helpful in some transdermal applications. However, over the long term (i.e., more than a few days) occluded skin becomes "macerated", that is the skin breaks down and becomes susceptible to infections, especially fungal. It would be advantageous to find a drug delivery system capable of delivering or a drug capable of being delivered transdermally without occlusion of the skin.

Many hormones, most notably progesterone, are not amenable to transdermal administration; due to low skin penetration high steroid dosages are necessary to maintain adequate blood levels. Sitruk-Ware et al, "Treatment of Benign Breast Diseases by Progesterone Applied Topically", In: *Percutaneous Absorption of Steroids*, Mauvais-Jarvis, et al., eds. London, England: Academic Press, pp. 219–229 (1980). The efficacy of natural progesterone is further decreased by its conversion in the skin to 5-α-dihydroprogesterone by 5-α-reductase. Mauvais-Jarvis et al., "In vivo Studies on Progesterone Metabolism by Human Skin", J. Clin. Endrocrinol. Metab., 29:1580–1585 (1969).

It has now been found that, unlike natural progesterone, topically applied synthetic progestin ST1435 diffuses through the skin to achieve pharmaceutically effective serum levels. This is unexpected since ST1435 is similar to progesterone in being degraded during hepatic first-pass metabolism and was consequently expected to be enzymatically degraded by 5-α-reductase in the skin. Topical application of ST1435 is thus suitable for contraception and any other indication for which ST1435 is an effective hormonal treatment. Furthermore, as shown in the examples provided below, ST1435 can be delivered transdermally in therapeutically effective amounts without occluding the skin.

SUMMARY OF THE INVENTION

Figure 1A:
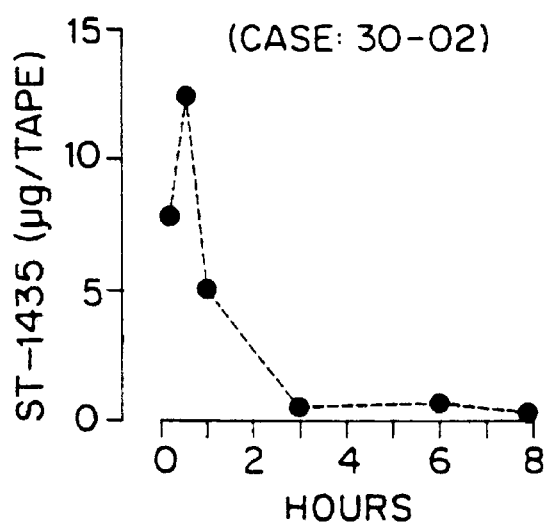
FIGS. 1(A and B) are graphs depicting the amount of ST1435 remaining on the skin after topical application.

According to applicants' invention, transdermal absorption of the synthetic progestin ST1435 has now been shown to result in therapeutically effective serum steroid concentrations. The concentration of ST1435 in serum remains high 24 hours after application, reflecting sustained release of the steroid through skin. Topical application of ST1435 offers an alternative to systemic progestin treatment in treatment of various gynecological problems and as a contraceptive. ST1435 is delivered transdermally in therapeutically effective amounts without occluding the skin.

DETAILED DESCRIPTION OF THE INVENTION

It has now been found that unlike natural progesterone, which is relatively ineffective when applied topically due to low penetration and rapid metabolism, low levels of the synthetic progestin ST1435 can be administered topically to achieve therapeutically effective, contraceptive levels of the hormone. When subdermal implants were tested, the concentration of ST1435 effective to function as a contraceptive was achieved at serum levels of between 50–100 pg/ml corresponding to 139–278 pmol/l. Lahteenmaki et al., "Pituitary and Ovarian Function During Contraception With One Subcutaneous Implant Releasing a Progestin ST1435", Contraception, 25:299–306 (1982).

The synthetic progestin ST1435 has been used mainly for contraceptive purposes. Coutinho, et al., "Fertility Control with Subdermal Silastic Capsules Containing a New Progestin (ST1435)", Int. J. Fertil., 21:103–108 (1976); and Lahteenmaki et al., "Contraception with Subcutaneous Capsules Containing ST1435. Pituitary and Ovarian Function and Plasma Levels of ST1435", Contraception, 23:63–75 (1981). ST1435 is further comparable to progesterone in showing a high relative binding affinity to human endometrial progesterone receptors. Additionally, ST1435 has not been found to exhibit side effects. Lahteenmaki et al., "Contraceptive Action of a Synthetic Progestin, ST1435", Thesis, University of Helsinki, Helsinki, Finland, pp. 35–36 (1986).

ST1435 has other non-contraceptive uses. For instance, ST1435 is more effective than natural progesterone in the treatment of benign breast disease, since the recommended daily dose of progesterone (via Progestogel®) is approximately 50 times the level of ST1435 required for contraception.

Due to rapid first-pass metabolism, ST1435, like natural progesterone, is ineffective when given orally. Although it has previously been shown that therapeutic serum levels can be achieved by parenteral administration from subcutaneous implants or vaginal rings there is no evidence that ST1435 would be effective when transdermally administered. Lahteenmaki, "Intestinal Absorption of ST1435 in Rats", Contraception, 30:143–151 (1984). In fact, it was expected that ST1435 would be degraded in the skin by 5-α-reductase as is progesterone.

It has now been shown that topically applied ST1435 is absorbed through the skin as early as two hours after the initial application. It has also been found that topical application of 1.5 mg–3.5 mg ST1435 per day is effective to inhibit ovulation.

Any pharmaceutically acceptable liquid or semisolid can be used in the present invention as a vehicle for ST1435 transdermal application, provided that ST1435 is sufficiently soluble in the vehicle to assure skin penetration of a therapeutically effective amount of ST1435. Any ST1435 that is not miscible in the vehicle would provide a reservoir of the hormone for continual release. There are a number of pharmaceutically acceptable vehicles suitable for use in the present invention including but not limited to creams, ointments, oils, gels, lotions and rinses. Descriptions of suitable vehicle formulations may be found in the *Physician's Desk Reference* Medical Economics Co. Pub., Oradell, N.J.

In transdermal administration of ST1435 via a transdermal device any pharmaceutically acceptable device is suitable for use according to the present invention, provided that therapeutically effective amounts of ST1435 can be delivered from the device. Suitable transdermal devices include but are not limited to bands, disks, bracelets or adhesive patches. Particularly preferred are the transdermal devices which are the subject matter of applicants' concurrently filed U.S. application Ser. No. 07/532,216 now abandoned. Said application is incorporated herein by reference. As it has now been found that ST1435 is therapeutically effective when applied topically in the absence of any occlusion of the skin, it is preferred that delivery of ST1435 be obtained by methods which do not cause occlusion of the skin. Particularly preferred vehicles are those which do not occlude the skin for instance creams, lotions, rinses, gels etc. or the transdermal device described in U.S. patent application Ser. No. 07/532,216 now abandoned to Moo-Young et al.

Surprisingly, it has now been found that transdermal devices with an in vitro release rate of up to 1 mg ST1435 per day are insufficient to inhibit ovulation, whereas those with a release rate of approximately 1.5 mg–3.5 mg ST1435 per day were effective in inhibiting ovulation.

Topical applications containing ST1435 may also include other hormones such as estrogens for treatment of various gynecological problems and/or as a contraceptive. The following examples are meant to illustrate but not limit the present invention.

EXAMPLE 1

ST1435 Skin Residue Study

Two volunteers, case 30-02 and case 19-02, each applied a single application of 1 mg ST1435 (previously ground with a mortar and pestle) in 0.1 ml Acetulan (Americhol. Corp. New Jersey) to an area of 10 cm×10 cm of the periumbilical skin. A polystyrene tray 12 cm×12 cm with 6 perforations each of 2 cm×3 cm was applied on top of the area to which the suspension was administered.

After 10 minutes, a strip of adhesive tape (1.8 cm×2.0 cm) was applied to one of the perforations in the polystyrene tray. After one minute, the tape was removed, stored and protected from light, and then analyzed for ST1435 concentration by radioimmunoassay (RIA) as described by Lahteenmaki et al. (1981) ibid. The same procedure using adhesive tape was then repeated after 30 minutes, 1 hour, 3 hours, 6 hours and 8 hours, except that each time the tape was applied to a different perforation in the polystyrene tray.

Figure 1B:
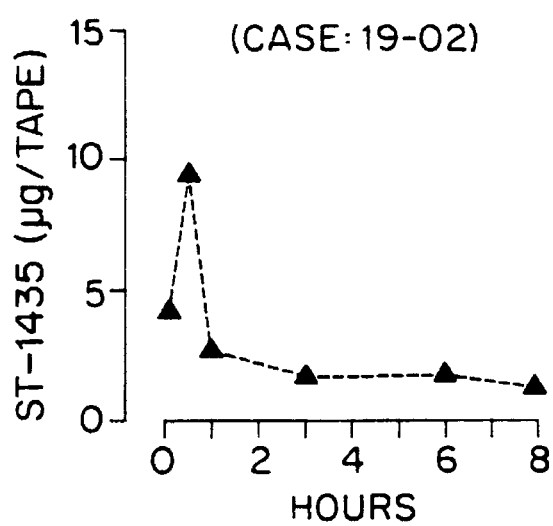

The amounts of ST1435 in the adhesive tapes for both volunteers are shown in FIGS. 1A and 1B. In both FIGS. 1A and 1B, the highest ST1435 values were attained at about 30 minutes after application of the ST1435 suspension, followed by a rapid decline to near baseline at 3 hours in case 30-02 (FIG. 1A). In case 19-02, ST1435 concentrations remained at an elevated level up to 8 hours when the last sample was taken (FIG. 1B).

EXAMPLE 2

ST1435 Contraceptive Cream Inhibits Ovulation

Three different concentrations of ST1435 were tested for their ability to inhibit ovulation. In all three the ST1435 was ground with a mortar and pestle and mixed with Acetulan. Mixture A was 100 mg ST1435 in 10 ml Acetulan; mixture B was 100 mg ST1435 in 5 ml Acetulan and mixture C was 500 mg in 10 ml Acetulan. Mixture A was a solution, mixtures B and C were suspensions.

By measuring plasma progesterone levels of volunteers after application of ST1435 it was determined that topically applied ST1435 suppresses ovulation. Four different regimens were followed: (a) 0.1 ml of mixture A containing 1 mg ST1435 applied three times per week; (b) 0.1 ml of mixture B containing 2 mg ST1435 applied three times per week; (c) 0.1 ml of mixture C containing 5 mg ST1435 applied three times per week; and (d) 0.1 ml of mixture B containing 2 mg ST1435 applied daily. The mixtures were applied to the periumbilicus in a 10 cm×10 cm area. The volunteers were tested over a control, nontreatment, menstrual cycle and a test, treatment menstrual cycle.

The results are summarized in Table 1 which shows the presumptive suppression of ovulation by topical administration of ST1435. A suppression of ovulation is presumed when there is no rise in progesterone at the expected luteal phase. Urinary LH and plasma progesterone were measured by RIA according to the World Health Organization (WHO), "The WHO Programme for the Standardization and Quality Control of Radioimmunoassay of Hormones in Reproductive Physiology", Horm. Res. (1978) 9:440–449. In Table 1 "Cycles" are the number of cycles studied and "Suppression" indicates the number of cycles eliciting progesterone suppression.

TABLE 1

| ST1435 Suppression of Progesterone Rise in the Expected Luteal Phase | | |
|---|---|---|
| Dose | Cycles | Suppression |
| 1 mg 3 times/week | 7 | 1 |
| 2 mg 3 times/week | 7 | 1 |
| 5 mg 3 times/week | 6 | 5 |
| 2 mg daily | 15 | 15 |

The results presented in Table 1 indicate that the three times weekly application of 1 mg or 2 mg of ST1435 failed to suppress plasma progesterone. However, the three times weekly application of 5 mg of ST1435 resulted in the suppression of plasma progesterone in 5 of the 6 cycles studied. Daily application of 2 mg of ST1435 suppressed plasma progesterone levels in all of 15 cycles studied.

Figure 2A:
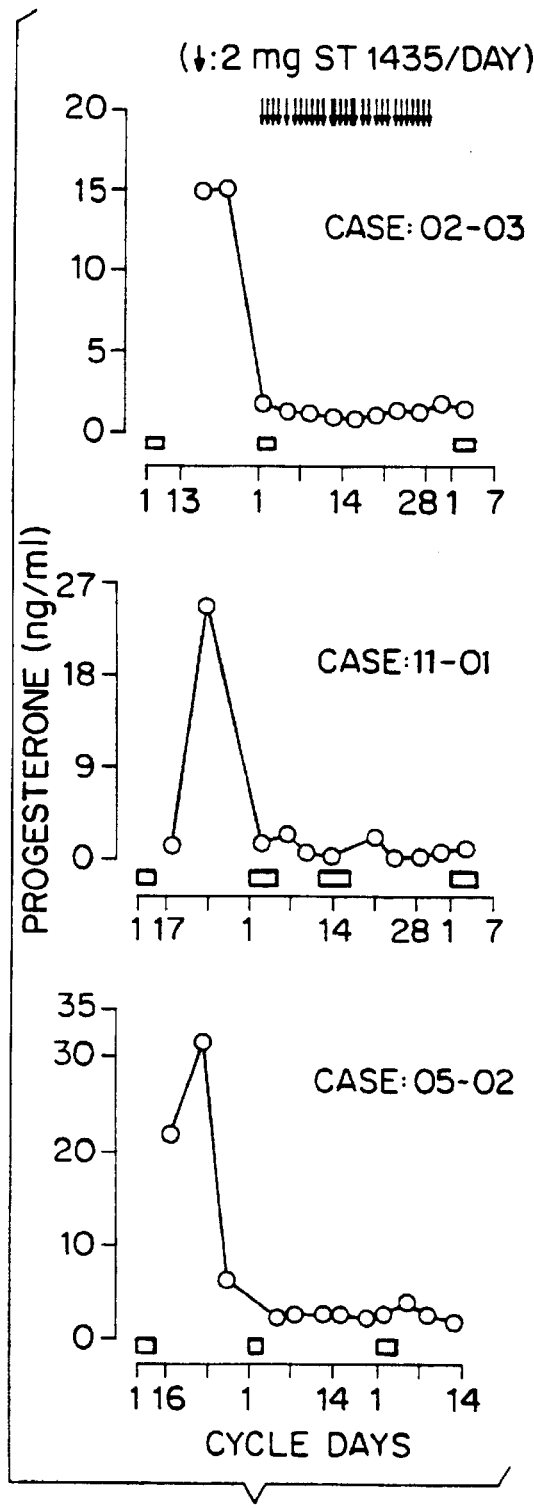
FIGS. 2(A and B) are graphs of typical plasma progesterone profiles before and during ST1435 treatment.
Figure 2B:
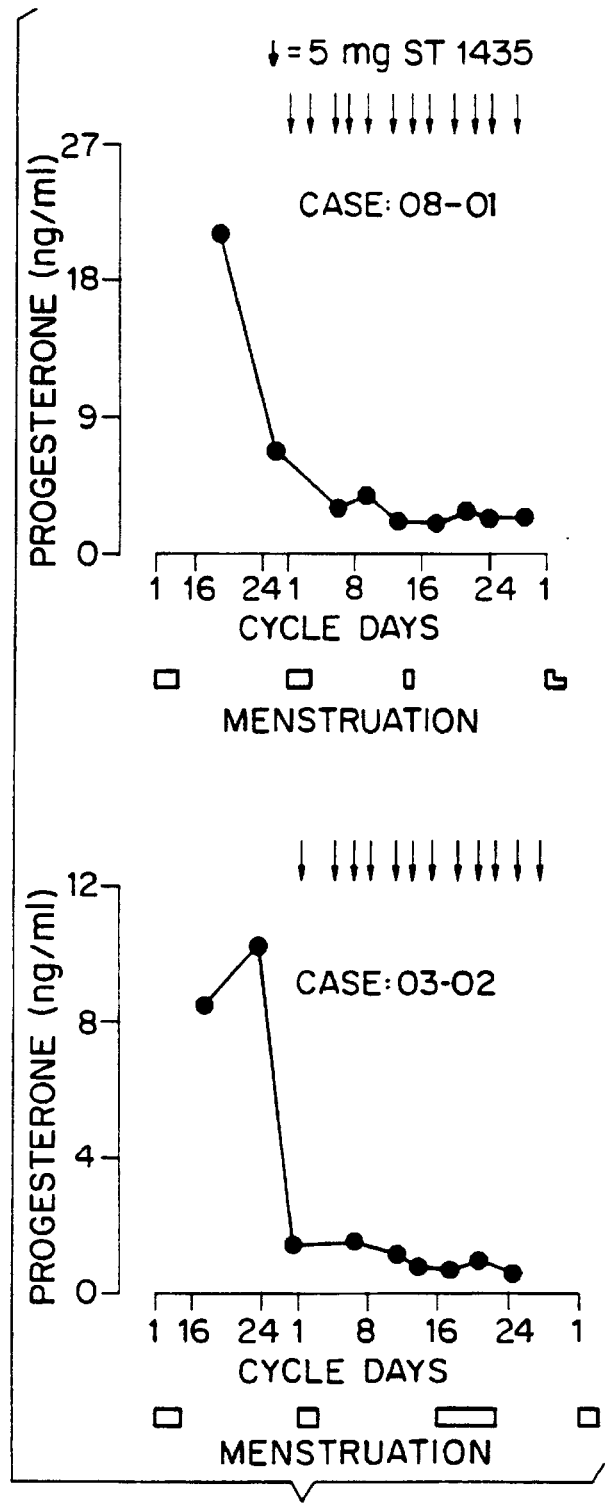

Plasma progesterone levels before and after ST1435 treatment are shown in FIGS. 2A and 2B. FIG. 2A shows the effect of daily application of a cream containing ST1435 (2 mg/application). Each of the three subjects apparently ovulated in the control, non-treatment, cycle as evidenced by high plasma progesterone levels prior to the menstrual bleeding that preceded the treatment cycle. Plasma progesterone levels were markedly suppressed during the treatment cycle. Menstruation is designated by the open box.

FIG. 2B shows the effect of application of a cream containing ST1435 applied three times a week (5 mg/application). Each of the two subjects apparently ovulated in the control cycle as evidenced by the high plasma progesterone levels prior to the one menstrual cycle that preceded the treatment cycle. Plasma progesterone levels were markedly suppressed during the treatment cycle.

EXAMPLE 3

ST1435-Acetulan Inhibits Ovulation

This example presents echographic evidence that the follicular cycle during treatment with ST1435 involves growth and atresia, rather than growth, rupture and luteinization, further verifying the contraceptive effect of ST1435. Additionally, assessments were made of the levels of ST1435 and progesterone in plasma, the levels of luteinizing hormone (LH) and sex steroid metabolites in urine, the bleeding patterns and the side effects associated with topical administration of 2 mg ST1435 administered per day during one cycle.

The study included one pretreatment cycle, one treatment cycle and one post-treatment cycle. First morning urine was collected daily for hormone assays. Three blood samples were taken during the luteal phase of the pretreatment cycle, and two samples were taken twice weekly during the treatment and post-treatment cycles. During the treatment cycle, each volunteer applied 2 mg ST1435 in 0.1 ml Acetulan daily to the skin from day 2 to day 28 of the cycle. The volunteer's ovaries were examined by ultrasound during all three cycles. Two volunteers were involved in this study. The ST1435/Acetulan was prepared as in Example 2.

Figure 3A:
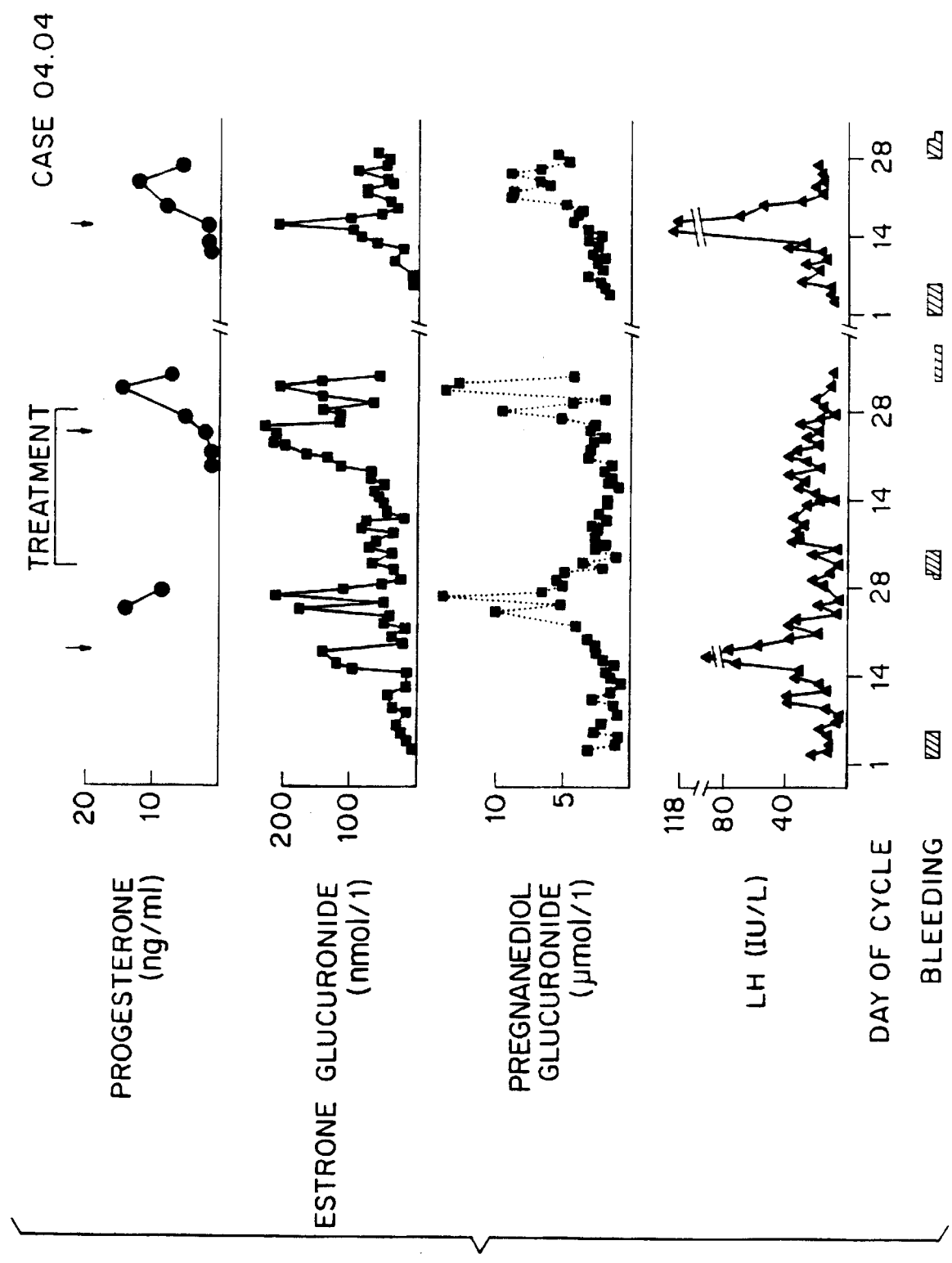
FIGS. 3(A and B) are graphs depicting hormone levels, follicular and menstrual cycles before, during and after treatment with ST1435 in Acetulan.
Figure 3B:
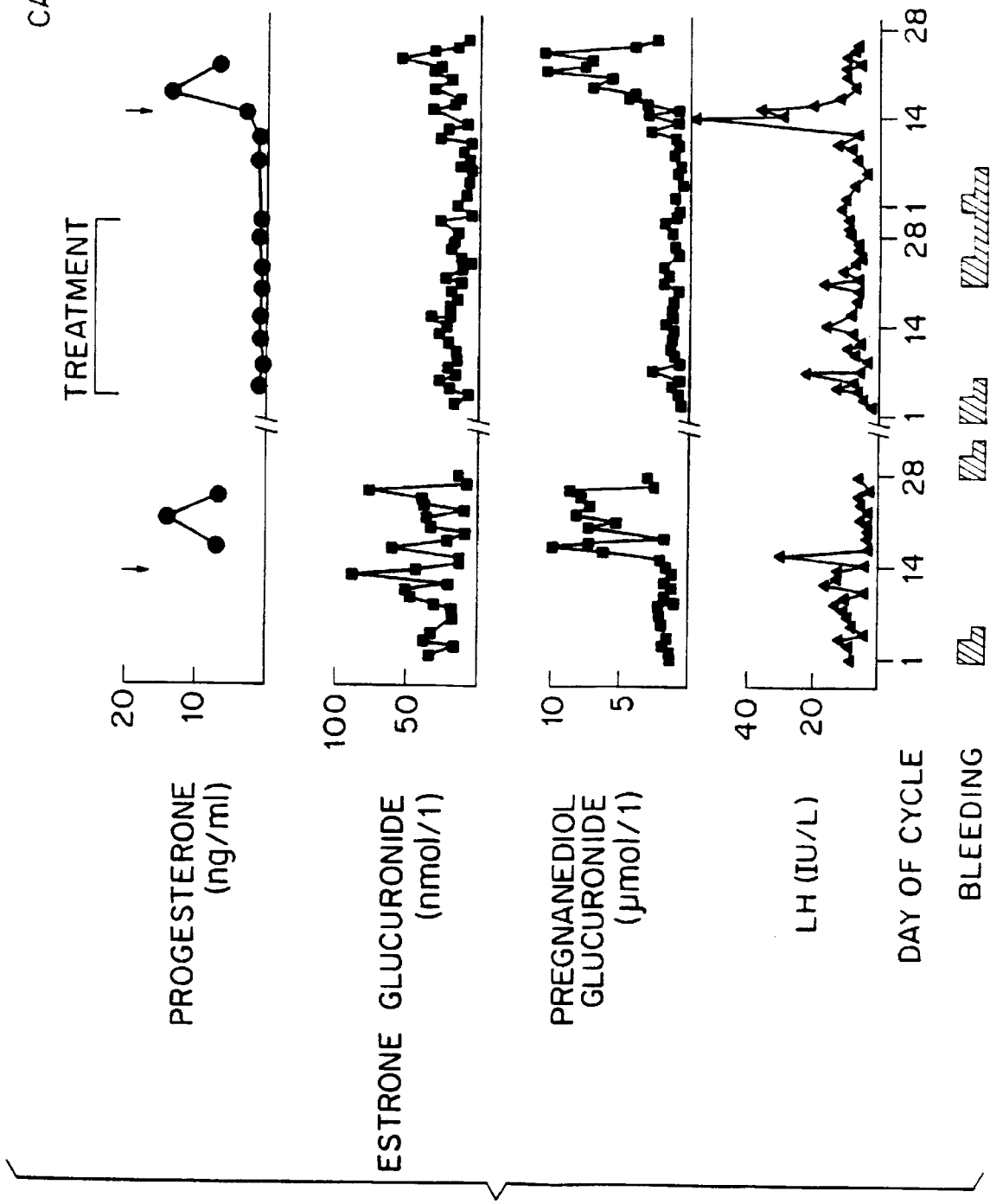

The results depicted in FIGS. 3A and 3B indicate that both subjects displayed rises in plasma progesterone, urinary pregnanediol, estrone glucuronides and LH. Hormone levels were determined by RIA according to WHO. The echographic evidence of follicular rupture in the pretreatment cycles were indicative of a normal ovulatory cycle. The arrows in FIGS. 3A and 3B indicate days on which follicular rupture occurred. For volunteer 04.04, the maximal follicular sizes before rupture were 21×17×23 mm on day 15 and 18×29×23 mm on day 10.

As seen in FIG. 3A, subject 04.04 had a late plasma progesterone rise (day 30) without a urinary LH peak during the treatment cycle. Echographic observation showed the presence of a follicle 27×23×21 mm, which ruptured on day 24 of the cycle. During the post-treatment cycle, a follicle 23×17×25 mm ruptured on day 15 and was followed by a rise in plasma progesterone. The bleeding pattern was undisturbed.

As shown in FIG. 3B, subject 13.03 did not show any rise in plasma progesterone, urinary LH, estrone and pregnanediol glucuronides during the treatment cycle. There was no evidence of follicular growth from day 8 to day 22 of the cycle. Follicular growth was observed in the post-treatment cycle, a follicle measuring 16×18×16 mm ruptured on day 11 followed by an ovulatory endocrine profile. There was evidence of a disturbed bleeding pattern.

EXAMPLE 4

Absorption of ST1435 Suspended in Progestogel®

This study determines the comparative rates of absorption of progesterone and ST1435 through the periumbilicus skin utilizing a formulation of 100 mg ST1435 suspended in 100 g of a gel containing 1 g of progesterone. Progestogel® is commercially available in France from Laboratoires Besins-Iscovesco and contains 10 mg of progesterone per 1.0 g of gel vehicle. ST1435 was simply stirred into the Progestogel®. Sufficient gel, containing 4.5 mg of ST1435 and 45 mg of progesterone; or 9.0 mg of ST1435 and 90 mg progesterone, was applied to the periumbilicus in a 20 cm×20 cm area. Tests were performed on two subjects during the last week of the menstrual cycle to avoid bleeding disturbances.

After application of the ST1435/progesterone gel, blood and saliva samples were collected and the ST1435 was measured by RIA according to Lahteenmaki et al. (1981) ibid. The results obtained are shown in FIGS. 4A and 4B depicting progesterone profiles in blood and saliva resulting from percutaneous applications of 9 mg ST1435 and 90 mg progesterone and 4.5 mg ST1435 and 45 mg progesterone, respectively.

Figure 4A:
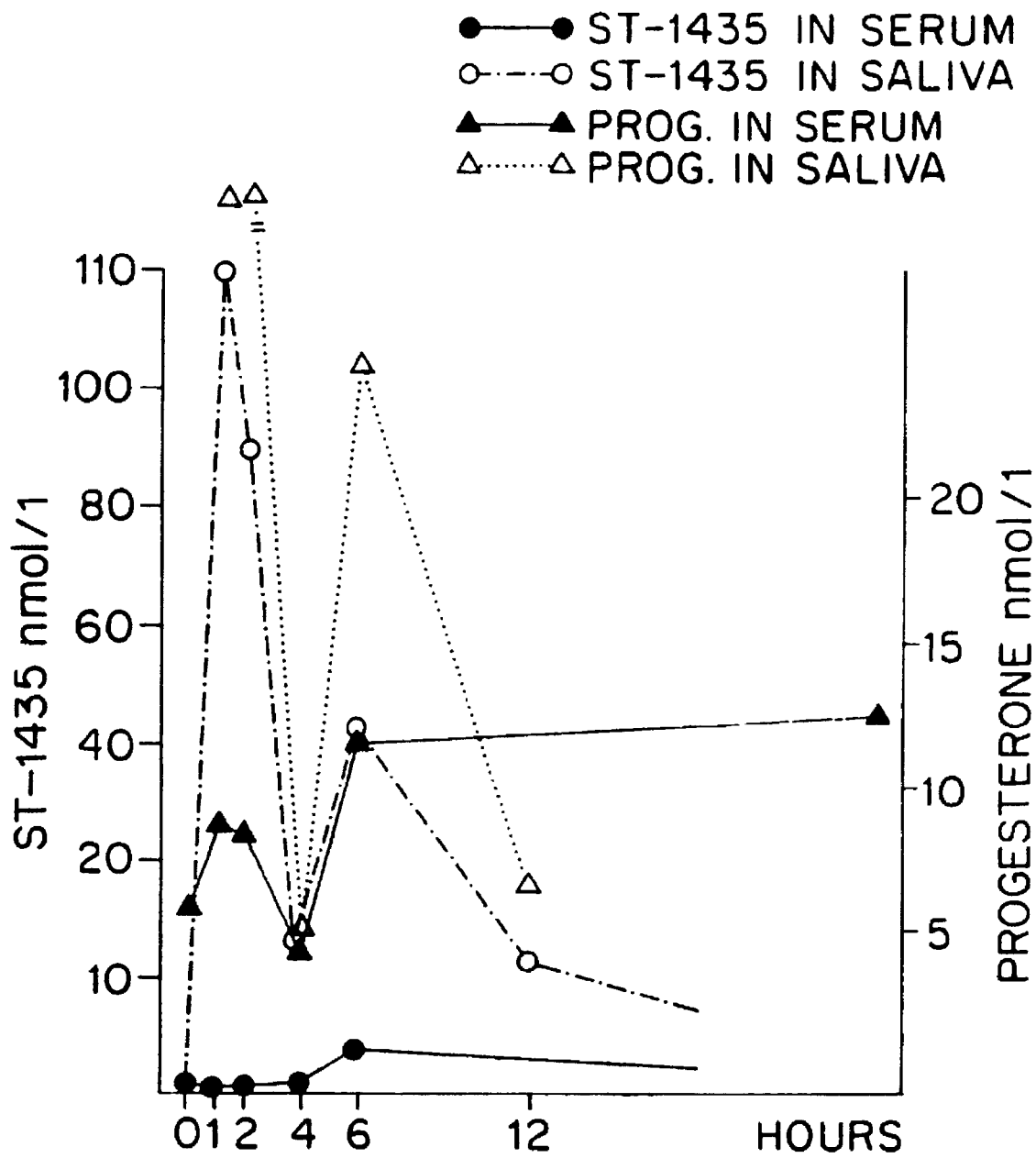
FIGS. 4(A and B) are graphs depicting the levels of ST1435 and progesterone in serum and saliva after treatment with ST1435 in Progestogel®.
Figure 4B:
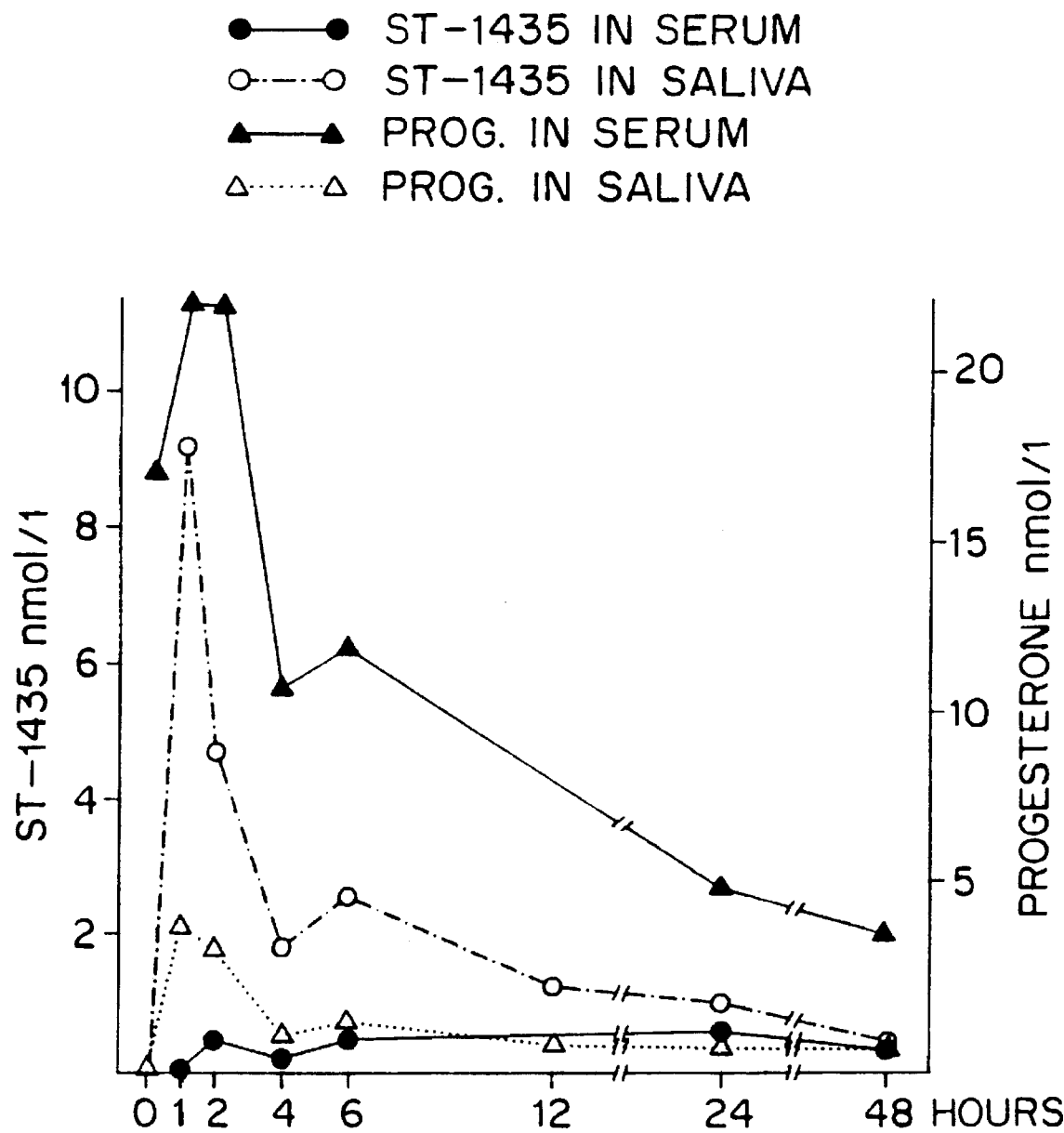

As shown in FIGS. 4A and 4B, both progesterone and ST1435 are clearly absorbed through the skin, as evidenced by the levels found in the saliva and blood of the two subjects. The levels of ST1435 found in the blood are sufficient to suppress ovulation, based on the blood levels of ST1435 found in patients where ovulation was suppressed with ST1435 subdermal implants, where the blood level of ST1435 was about 2 to 3 times less than those shown in FIGS. 4A and 4B.

It should be noted, that maximal serum levels were observed approximately 6–24 hours after gel application.

EXAMPLE 5

Topical Application of ST1435 in Progestgel®

Six healthy women with regular menstrual cycles participated voluntarily in this study. The experiments were carried out during the luteal phase of the menstrual cycle to avoid bleeding disturbances. "Progestogel®" was used as the vehicle. The concentration of progesterone in Progestogel® is 10 mg per 1.0 g of vehicle and the recommended therapeutic dose is 5 ml per day. ST1435 was incorporated into Progestogel® without difficulty at concentrations of 0.5 and 1.0 mg per 1.0 g of vehicle. The concentrations of ST1435 were 5 and 10% of that of progesterone in the Progestogel®. A 5 ml applicator was used to dispense the gel, which was applied to the periumbilical area.

A single 5 ml dose of gel was applied to each of three women at 8 a.m. The doses contained 2.3, 4.5 and 9 mg of ST1435, each woman receiving a different dose. Saliva (1–2 ml) and blood samples were collected at the following time intervals after application: 0, 1, 2, 4, 6, 24 and 48 hours. In three other women, gel containing 2.3 mg of ST1435 was applied at 8 p.m. at home for five days and the samples were collected 12 hours later at 8 a.m. for 6 days. Serum was separated from venous blood samples by centrifugation. Additional samples of saliva were collected at fixed times at home. The samples were stored at −20° C. until analyzed by RIA.

The concentrations of ST1435 in samples of serum and saliva were determined by RIA essentially as described previously by Lahteenmaki et al., (1981) ibid. The practical detection limit of the ST1435 by RIA was 30 pmol/l. The concentrations of progesterone were also measured by RIA as provided by WHO (1978) ibid.

The purity of the ST1435 measured in serum and saliva was determined by fractionating pooled patient samples on thin layer chromatography (TLC) or LH-20 column chromatography. The patient samples and blank serum containing unlabeled ST1435 were extracted with petroleum ether. For TLC the extracts were thereafter chromatographed on Kieselgel F 254 (Merck, Darmstadt, West Germany) using a solvent system of hexane:ethyl acetate:methanol [90:5:5]. The TLC was cut into slices of 5 mm, eluted with methanol and the RIA for ST1435 was performed on the eluate as described by Lahteenmaki et al., (1981) ibid. The LH-20 column (Sephadex LH-20, Pharmacia, Uppsala, Sweden) chromatography was performed as described by Lahteenmaki, (1984) ibid. One ml fractions were collected and the ST1435 content was assayed with RIA. The correlation coefficients between the paired samples of serum and saliva were calculated with the Stat Works statistical software (Cricket Software, Inc., Phila. Pa.).

Table 2 shows the ST1435 and progesterone (P) levels (pmol/l) obtained in serum over time in response to various doses of ST1435. According to these results, therapeutic serum levels were obtained within four hours after gel application. Moreover, the serum concentration of ST1435 remained at this level for 24 hours, indicating sustained release of the steroid from the skin. At 48 hours after gel application the serum concentration had decreased to low but measurable levels.

TABLE 2

| | Concentrations (pmol/l) of ST1435 and Progesterone (P) in Serum | | | | | |
|---|---|---|---|---|---|---|
| Hours | 2.3 mg ST1435 | P | 4.5 mg ST1435 | P | 9.0 mg ST1435 | P |
| 0 | 0 | 2.0 | 0 | 17.4 | 0 | 7.4 |
| 1 | 48 | 2.4 | 63 | 22.5 | 129 | 9.1 |
| 2 | 71 | 2.6 | 445 | 22.5 | 327 | 8.9 |
| 4 | 83 | 3.6 | 190 | 11.3 | 411 | 5.5 |

TABLE 2-continued

| | Concentrations (pmol/l) of ST1435 and Progesterone (P) in Serum | | | | | |
|---|---|---|---|---|---|---|
| Hours | 2.3 mg ST1435 | P | 4.5 mg ST1435 | P | 9.0 mg ST1435 | P |
| 6 | 101 | 3.1 | 466 | 12.2 | 378 | 11.7 |
| 24 | 232 | 5.6 | 438 | 5.2 | 694 | 12.2 |
| 48 | 59 | 11.4 | 112 | 3.7 | — | — |

During treatment for five days in three women at a dose of 2.3 mg of ST1435 per day, varying serum steroid concentrations were found, reflecting individual variation. Thus the serum ST1435 levels were three times as high in subject 3 as in subject 1. These serum samples were taken 12 hours after gel application and show that therapeutic levels are obtained with this transdermal steroid dose. At 36 hours after gel application (data not shown), serum ST1435 concentrations were decreased but still in the effective range found during parenteral contraception with ST1435.

After gel application, concentrations of ST1435 were found to be high in saliva, especially during the first two hours after gel application. Table 3 shows that peak ST1435 concentrations in saliva were reached rapidly after gel application and before serum levels reached peak values.

TABLE 3

| | Concentrations of ST1435 (pmol/l) in Saliva After a Single Dose | | |
|---|---|---|---|
| | Dosage ST1435 (mg) | | |
| Hours | 2.3 | 4.5 | 9.0 |
| 0 | 0 | 0 | 0 |
| 1 | — | 9026 | 114900 |
| 2 | 71 | 4630 | 88900 |
| 4 | 87 | 1761 | 10000 |
| 6 | 158 | 2228 | 41480 |
| 12 | 103 | 1175 | 10200 |
| 24 | 82 | 813 | 2552 |
| 48 | 0 | 216 | — |

Comparing Tables 2 and 3 it can be seen that the concentration of ST1435 in saliva was roughly ten times as high as in serum. However, following a single dose application the salivary excretion was not correlated with serum levels (r=0.072; p=0.77). During treatment for five days, the concentration of ST1435 in saliva was higher in samples taken 12 hours compared to 24 hours after gel application showing dependence on repeated dosage. In the simultaneously collected samples of serum and saliva, the concentrations of ST1435 were statistically significantly correlated (r=0.683, p<0.001).

The concentrations of progesterone in serum and saliva were also determined. Endogenous progesterone secretion interferes with and cannot be eliminated from the results. As seen from Table 2 the serum concentrations of progesterone did not differ greatly from the control levels observed before gel application (0 hour). This may reflect luteal function more than a contributory exogenous transdermal progesterone. In the three women treated for five days, serum progesterone concentrations were slightly elevated, possibly as a result of the gel treatment. Serum progesterone and ST1435 levels were not correlated, as could be expected from the experimental design.

The RIA of ST1435 has been shown to be specific for ST1435. Metabolites of ST1435 do not appear to interfere, because 90–100% of the RIA measurable steroid was chromatographically identical to intact ST1435. Following fractionation on TLC or LH-20 column chromatography, >95% of the measurable ST1435 appeared in a single spot. Moreover, the behavior of ST1435 was identical in patient samples when compared to unlabeled ST1435. These data indicate that ST1435 is not metabolized and that effective levels of ST1435 are maintained by topical application of the steroid.

EXAMPLE 6

Comparison of Transdermal Absorption of two Hormones, ST1435 and Levonorgestrel

In order to compare the transdermal delivery of ST1435 with other steroids, ST1435 and levonorgestrel (LNG) were mixed into the same cream, applied to subjects and serum levels of the hormones measured. Although both hormones were absorbed into the blood stream, only ST1435 consistently achieved anovulatory serum levels. LNG achieved anovulatory serum levels in only one of four subjects tested.

ST1435 and LNG were ground with a mortar and pestle and equal amounts of each were mixed into the base gel used to make Progestogel® (Laboratoires Besins-Iscovesco France). The base gel does not contain any hormones. The final mixture contained 0.5 mg of each hormone per 1 g of gel. A dose of 5.0 ml of the gel was placed on a 10×10 cm area of each of four healthy normal weight women volunteers during the late luteal phase. Blood samples were collected at 0, 30 min., 1, 2, 4, 6, 24, and 48 hours and the concentrations of the hormones were measured by RIA as described in Example 1. Note that the concentrations are in pmol/l.

TABLE 4

| Serum Levels of ST1435 and LNG after Simultaneous Transdermal Application | | | | |
|---|---|---|---|---|
| Subject | Sample | Time Hours | ST1435 pmol/l | LNG pmol/l |
| MH | 1 | 0 | 0 | 0 |
| | 2 | 0.5 | 7 | 0 |
| | 3 | 1 | 43 | 13 |
| | 4 | 2 | 52 | 64 |
| | 5 | 4 | 66 | 26 |
| | 6 | 6 | 86 | 93 |
| | 7 | 24 | 44 | 226 |
| | 8 | 48 | 36 | 140 |
| AR | 1 | 0 | 0 | 0 |
| | 2 | 0.5 | 0 | 0 |
| | 3 | 1 | 0 | 0 |
| | 4 | 2 | 60 | 137 |
| | 5 | 4 | 118 | 147 |
| | 6 | 6 | — | 131 |
| | 7 | 24 | 6 | 217 |
| | 8 | 48 | 38 | 348 |
| HR | 1 | 0 | 0 | 0 |
| | 2 | 0.5 | 208 | 0 |
| | 3 | 1 | 226 | 13 |
| | 4 | 2 | 181 | 61 |
| | 5 | 4 | 160 | 61 |
| | 6 | 6 | 298 | 77 |
| | 7 | 24 | 625 | 677 |
| | 8 | 48 | 364 | 585 |
| MT | 1 | 0 | 10 | 0 |
| | 2 | 0.5 | 16 | 26 |
| | 3 | 1 | — | 26 |
| | 4 | 2 | 18 | 32 |
| | 5 | 4 | 61 | 70 |
| | 6 | 6 | 169 | 63 |
| | 7 | 24 | 56 | 278 |
| | 8 | 48 | 36 | 214 |

For each subject represented in Table 3 serum ST1435 levels reached contraceptive levels within 4 hours whereas only in subject HR did LNG levels become high enough to be contraceptive and then only after 24 hours (677 pmol/l). ST1435 thus reaches an effective plasma level under conditions where LNG fails to do so.

EXAMPLE 7

ST1435 Delivered via a Transdermal Device

Figures 5A, 5B:
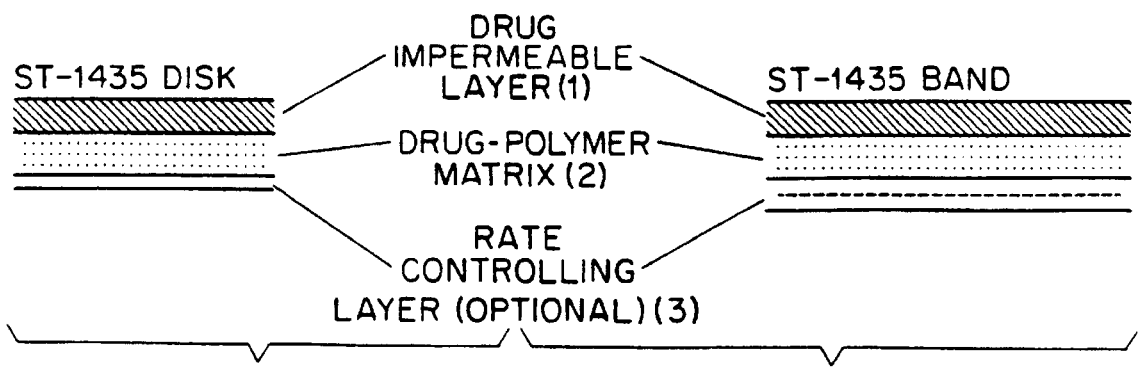
FIGS. 5(A and B) are cross sectional views of transdermal delivery systems for ST1435.

Two transdermal devices (i.e., using solid vehicles) were studied for transdermal delivery of ST1435. The first was a disk, about 3 cm in diameter with a 25% drug load in a drug-polymer matrix, and the second was a band, also containing a 25% drug load in drug polymer matrix. FIG. 5 depicts cross sectional views of these two ST1435 transdermal delivery systems, each containing a drug impermeable layer (1), and a drug-polymer matrix (2). The bands also contained a rate limiting membrane (3). These devices contained no enhancers or alcohol. There were no adhesive layers on the drug polymer matrices (2). Adhesive was used only on the backs of the drug impermeable layers (1) so that the devices could be attached to the back of a suitable article such as a wrist watch or a bracelet. Thus, the elements of conventional transdermal devices responsible for skin irritation, namely enhancers, alcohols and adhesives were either missing or placed so as to be removed from contact with the skin.

Figure 6A:
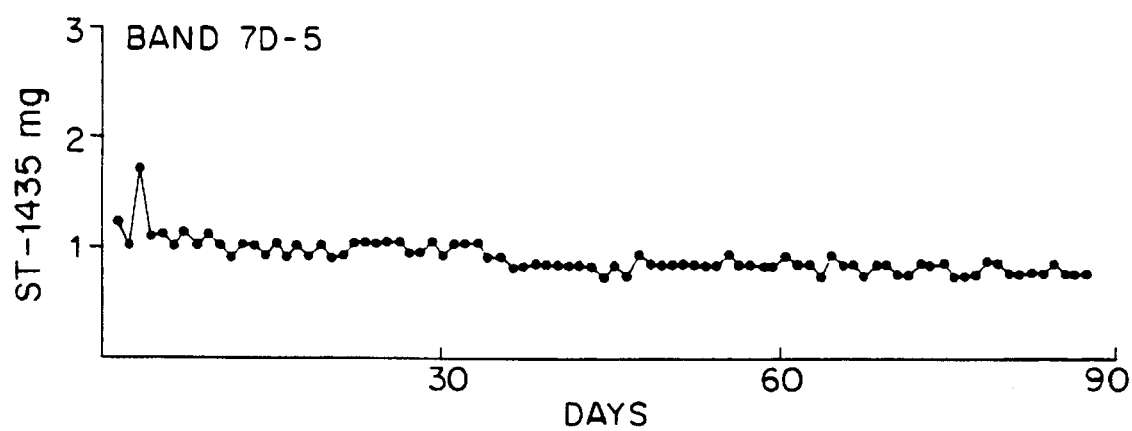
FIGS. 6(A and B) are graphs depicting in vitro release rates of ST1435 from a transdermal disk and a band.
Figure 6B:
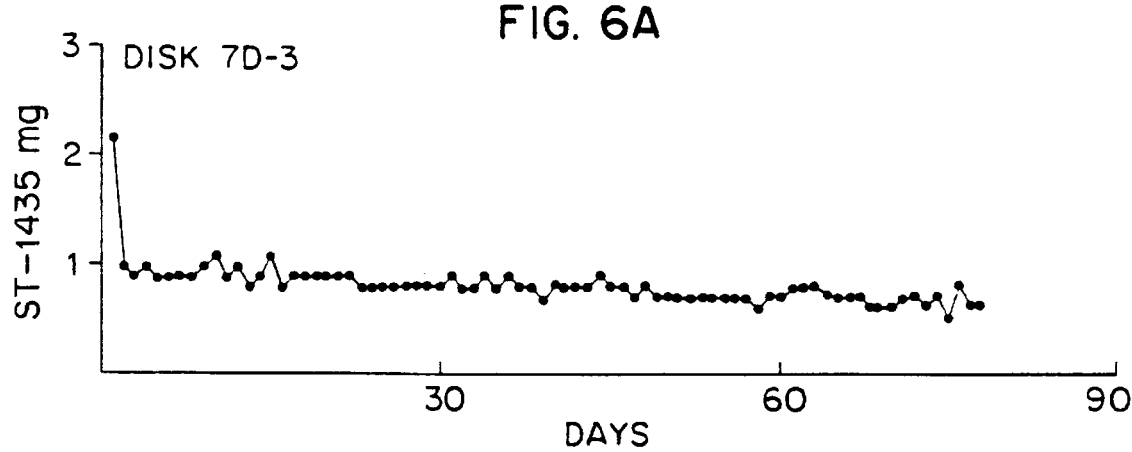

In vitro release rate studies using the disk and band described above indicated that after an initial burst, the disk released approximately 0.8 mg ST1435 per day for about 40 days, and somewhat less at 85 days. When tested in vitro, the band gave an initial release rate of about 1 mg ST1435 per day, which slowly decreased to about 0.8 mg per day at 90 days. These results are shown in FIG. 6.

The band was tested for one cycle in two volunteers. Ovulation inhibition was not accomplished, as plasma progesterone levels were not suppressed to anovulatory levels, consequently the disk was not tested clinically. Plasma progesterone levels were determined as described in Example 1.

Figure 7:
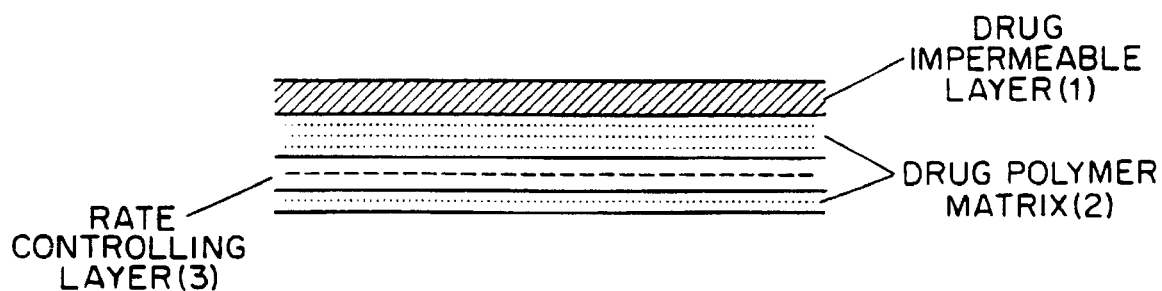
FIG. 7 is a cross sectional view of a transdermal drug delivery bracelet for ST1435.

A third transdermal delivery device was made which comprised a drug impermeable layer (1), and a rate limiting membrane (3) sandwiched between two layers of drug-polymer matrices (2) of different thicknesses. FIG. 7 shows a cross sectional view of this device. It contained no enhancers or alcohol and no adhesive on the drug releasing surface.

The third device was made as follows: 1402.5 mg of Medical Grade Elastomer 382 was mixed with 467.5 mg ST1435. Although Elastomer 382 is no longer commercially available, polymer MDF4-4210, a heat curable platinum catalyzed system, is a suitable substitute. Four drops of catalyst, (stannous octoate, Catalyst M from Dow Corning Corp.) were added according to the manufacturer's instructions. Two separate drug polymer matrix layers (2) of different thicknesses were formed by polymerization carried out in a 2 cm×7.5 cm×0.1 cm mold. A thin Teflon® lining was layered on the outer surface of the device as the drug impermeable layer (1) to prevent steroid diffusion in that direction. A perforated dialysis membrane was inserted as the rate limiting membrane (3) between the inner (thicker) drug-polymer matrix layer (2) and the outer (thinner) drug-polymer matrix layer (2) to slow steroid diffusion toward the drug releasing surface.

Before use the third device was incubated for 7 days in 600 ml of water at 37° C. with continuous agitation to obtain an estimation of the ST1435 in vitro release rate.

Figure 8:
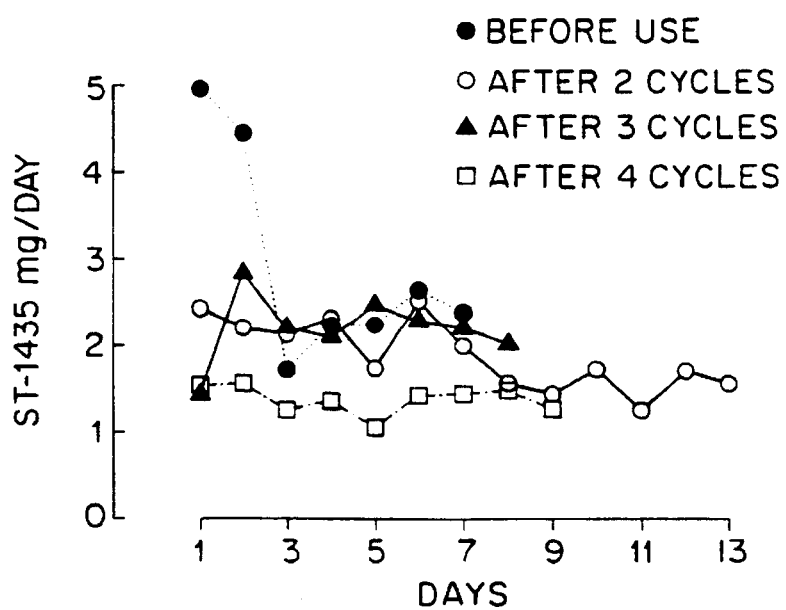
FIG. 8 is a graph depicting the in vitro release rates of ST1435 from a transdermal delivery bracelet, before use, and after 2 cycles, 3 cycles and 4 cycles of use.

The third device was tested on a bracelet for one cycle each on four healthy, normally menstruating women protected by sexual abstinence or by IUD (cases 13-02, 03-04, 31-01 and 40-01). The in vitro release rate of ST1435 from the bracelet was determined before use and after 2, 3 and 4 cycles of use. Before use, the bracelet released approximately 2–2.5 mg ST1435 per day, after an initial burst. After 2 cycles of use, the release rate was between 1.5 and 2.5 mg ST1435 per day; after 3 cycles of use, it was approximately 2.2 mg ST1435 per day and after 4 cycles of use it was 1.5 mg ST1435 per day. FIG. 8 shows the in vitro release rates of ST1435 from the third device bracelet, before use, after 2 cycles, 3 cycles and 4 cycles of use.

All four volunteers completed the study with the third device. Endocrine profiles obtained from the volunteers are shown in FIGS. 9A–9D. The endocrine profiles suggest that all subjects displayed ovulatory patterns during the control, pretreatment cycle. During the treatment cycle, urinary estrone glucuronide levels were elevated; however, pregnanediol glucuronide levels remained low. In three cases (13-02, FIG. 9A; 03-04, FIG. 9B; and 31-01, FIG. 9C), there were no LH peaks during the treatment cycle, whereas, in one case (40-01, FIG. 9D) an LH peak was observed at day 8; however, the peak was smaller than that observed in the pretreatment period. Progesterone levels were indicative of anovulatory cycles in 3 of the 4 cases. In case 13-02, one sample showed an elevated plasma level but this was not accompanied by an elevated pregnanediol glucuronide peak.

Figure 9A:
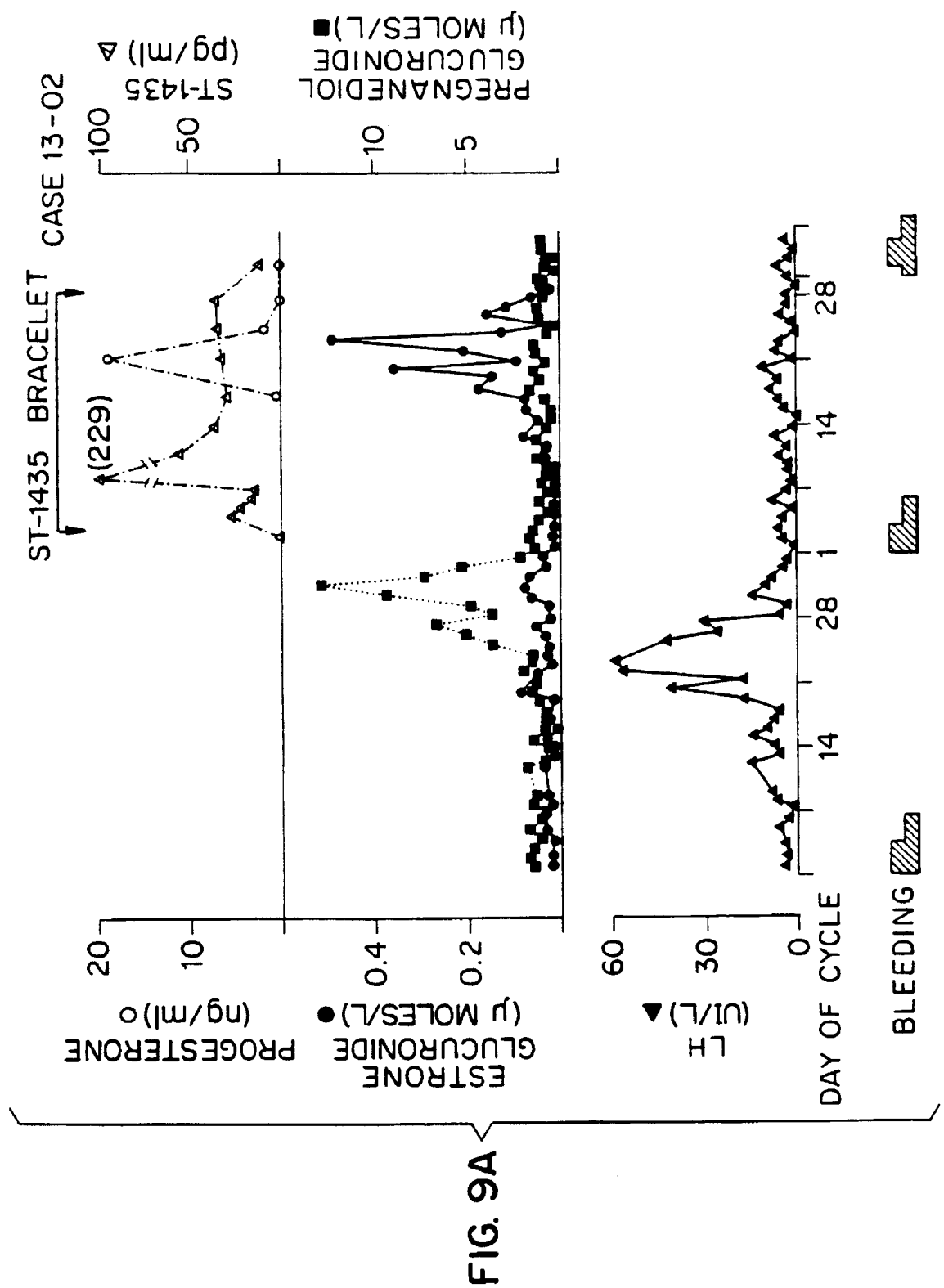
FIGS. 9(A-D) are graphs depicting endocrine profiles before and after treatment with a transdermal bracelet releasing ST1435.
Figure 9B:
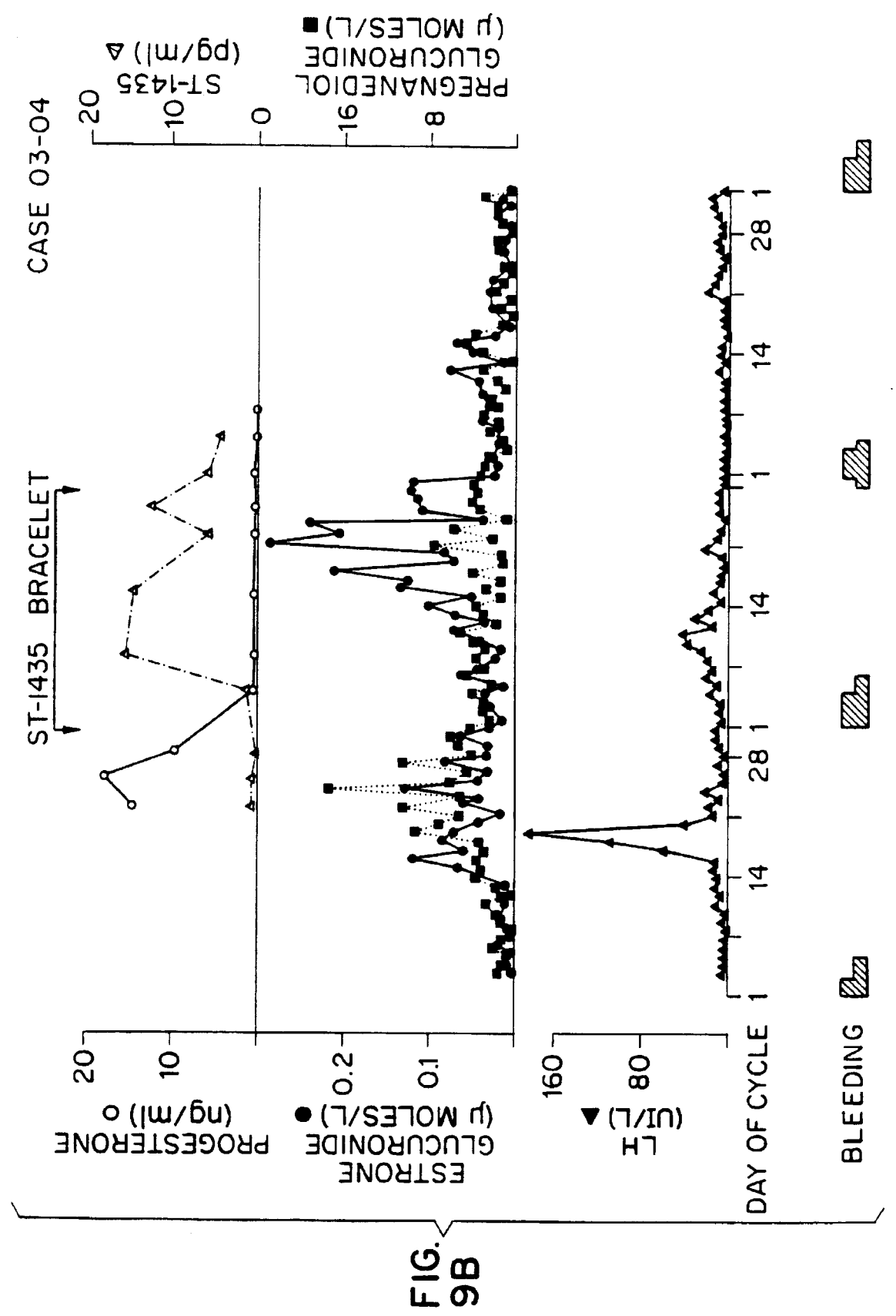
Figure 9C:
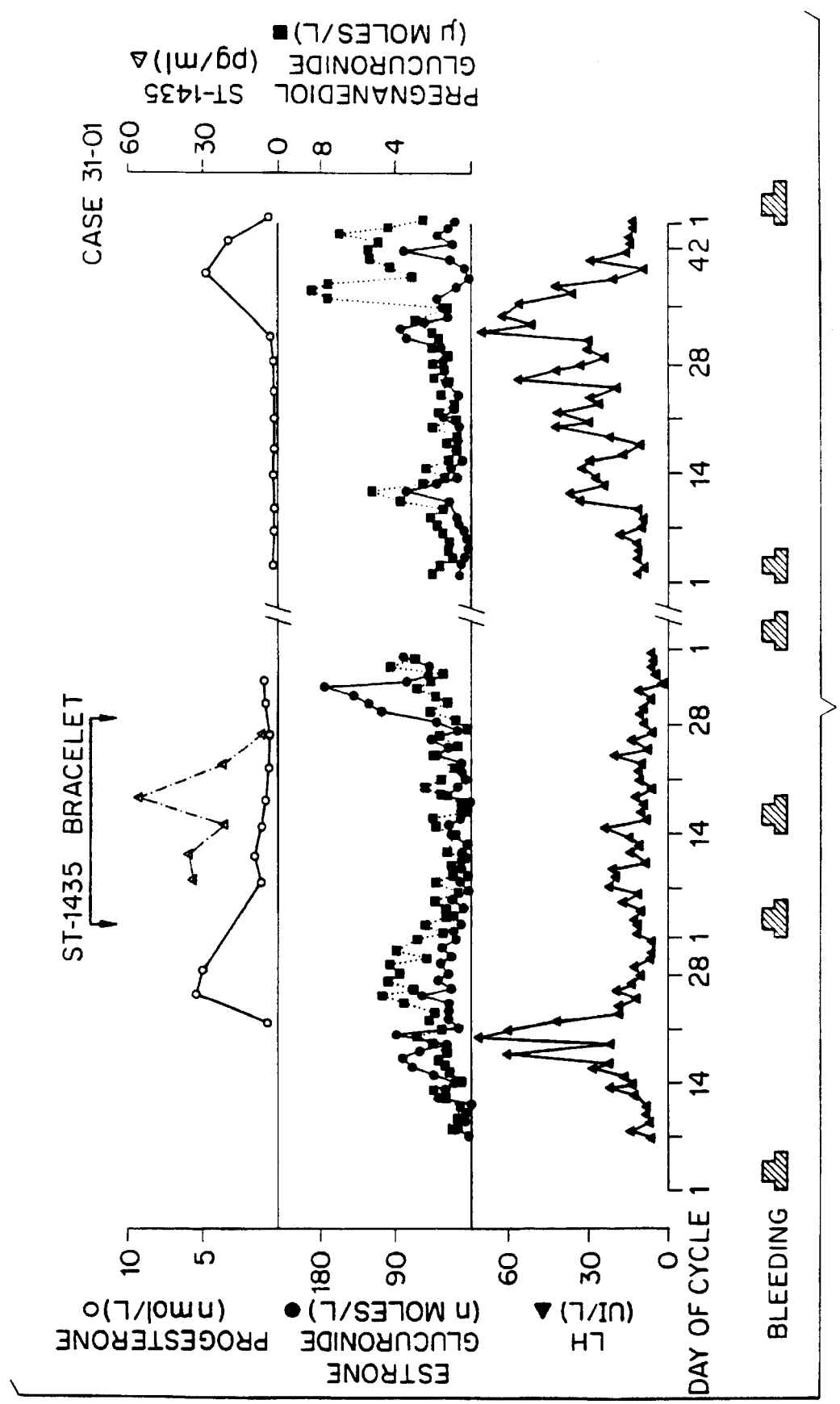
Figure 9D:
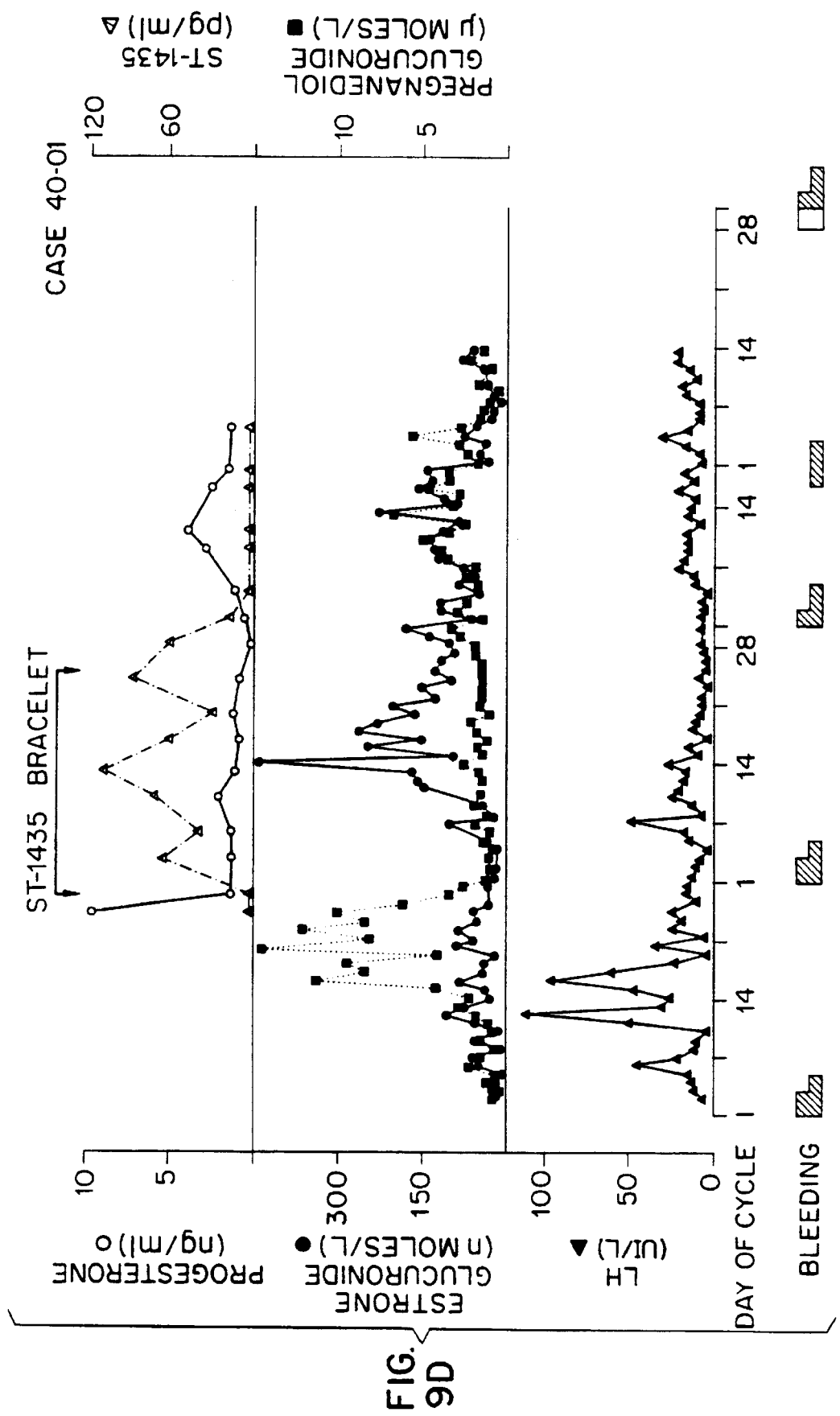

FIG. 9A shows a late progesterone peak during the treatment cycle that was not accompanied by elevated pregnanediol glucuronide or LH peaks. FIG. 9B shows that plasma levels of ST1435 were elevated. Progesterone levels during the pretreatment cycle were indicative of an ovulatory cycle whereas progesterone levels were markedly suppressed during treatment cycle. The post-treatment cycle was anovulatory. FIG. 9C shows pretreatment and post treatment profiles indicative of ovulatory cycles. The post treatment cycle also showed altered LH profiles and that ovulation was suppressed during treatment cycle.

Post treatment cycle in case 03-04 was anovulatory; in case 31-01 it was longer than normal with a disturbed LH pattern; in case 40-01 it was shorter than normal. The bleeding patterns in 3 of the treated cycles were undisturbed, whereas in case 31-01 there were breakthrough bleedings on days 14 and 19 respectively.

The data presented above show that ST1435 attain therapeutically effective levels after topical application. The method of topical application is unimportant, ST1435 can be applied alone or in combination with other steroids such as estrogens either in a liquid or semisolid formulation or in a solid form such as a transdermal device.

What is claimed is:

1. A topical composition for application of a compound 16-methylene-17α-acetoxy-19-nor-4-pregnene-3,20 dione to the skin of an individual, said composition comprising in admixture the compound and a pharmaceutical vehicle acceptable for topical application of the compound to the skin of the individual wherein said vehicle is selected from the group consisting of ointments, creams and gels, wherein the compound is present in the composition in an amount sufficient to attain a therapeutically effective amount of the compound in the serum of the individual upon topical administration of the composition.

2. The composition of claim 1 wherein the 16-methyl-17α-acetoxy-19-nor-4-pregnene-3,20 dione is present in the composition in an amount sufficient to attain a contraceptively-effective amount of the compound in the serum of the individual.

3. The composition of claim 1 wherein the 16-methylene-17α-acetoxy-nor-4-pregnene-3,20 dione is present in the composition in an amount sufficient to attain serum concentrations greater than about 50 pg/ml.

4. The composition of claim 1 further comprising a therapeutically effective amount of an estrogen.

5. The composition of claim 4 wherein the estrogen is selected from the group consisting of 17-β-estradiol, ethinylestradiol and mixtures thereof.

6. A method of topically administering a therapeutic amount of a compound 16-methylene-17α-acetoxy-19-nor-4-pregnene-3,20 dione to an individual comprising applying to the skin of the individual a topical composition comprising in admixture the compound and a pharmaceutical vehicle acceptable for topical application of the compound to the skin of the individual wherein said vehicle is selected from the group consisting of creams, ointments and gels, wherein the compound is present in the composition in an amount sufficient to attain a therapeutically effective amount of the compound in the serum of the individual upon topical administration of the composition.

7. The method according to claim 6 wherein the 16-methyl-17α-acetoxy-19-nor-4-pregnene-3,20 dione is present in the composition in an amount sufficient to attain a contraceptively-effective amount of the compound in the serum of the individual.

8. The method according to claim 6 wherein the 16-methylene-17α-acetoxy-nor-4-pregnene-3,20 dione is present in the composition in an amount sufficient to attain serum concentrations greater than about 50 pg/ml.

9. The method according to claim 6 wherein the composition further comprises a therapeutically effective amount of an estrogen.

10. The method according to claim 9 wherein the estrogen is selected from the group consisting of 17-β-estradiol, ethinylestradiol and mixtures thereof.

11. The method of claim 6 wherein the composition is topically applied to the skin of the individual in an area no greater than about 400 $cm^2$.

* * * * *